(12) United States Patent
Shivakumar et al.

(10) Patent No.: US 9,789,113 B2
(45) Date of Patent: Oct. 17, 2017

(54) PEMETREXED DIPOTASSIUM FORMULATIONS

(71) Applicant: SHILPA MEDICARE LIMITED, Karnataka (IN)

(72) Inventors: Pradeep Shivakumar, Vizianagaram (IN); Akshay Kant Chaturvedi, Raichur (IN)

(73) Assignee: SHILPA MEDICARE LIMITED, Raichur, Karnataka ( * ) Notice: Subject to any disclaimer, the term of this patent is extended or adjusted under 35 U.S.C. 154(b) by 0 days.

(21) Appl. No.: 15/310,451

(22) PCT Filed: Jun. 23, 2015

(86) PCT No.: PCT/IB2015/054675
§ 371 (c)(1),
(2) Date: Nov. 11, 2016

(87) PCT Pub. No.: WO2016/001792
PCT Pub. Date: Jan. 7, 2016

(65) Prior Publication Data
US 2017/0100403 A1    Apr. 13, 2017

(30) Foreign Application Priority Data
Jun. 30, 2014 (IN) .......................... 3169/CHE/2014

(51) Int. Cl.
*A01N 43/90* (2006.01)
*A61K 31/519* (2006.01)
*C07D 487/00* (2006.01)
*A61K 47/26* (2006.01)
*A61K 9/00* (2006.01)

(52) U.S. Cl.
CPC .......... *A61K 31/519* (2013.01); *A61K 9/0019* (2013.01); *A61K 47/26* (2013.01)

(58) Field of Classification Search
None
See application file for complete search history.

(56) References Cited

U.S. PATENT DOCUMENTS

| 6,686,365 | B2 | 2/2004 | Riebesehl et al. |
| 7,138,521 | B2 | 11/2006 | Chelius et al. |
| 8,088,919 | B2 | 1/2012 | Busolli et al. |
| 2015/0259348 | A1* | 9/2015 | Sharawat ............. C07D 487/04 514/265.1 |

FOREIGN PATENT DOCUMENTS

| CN | 1907284 A | 2/2007 | |
| CN | 101081301 A | 12/2007 | |
| CN | 101417998 A | 4/2009 | |
| CN | 102838602 A | 12/2012 | |
| WO | 2008021411 A2 | 2/2008 | |
| WO | WO2008/021411 | * 2/2008 | ........... C07D 487/04 |
| WO | 2010030598 A2 | 3/2010 | |
| WO | 2010031357 A1 | 3/2010 | |
| WO | 2012015810 A2 | 2/2012 | |
| WO | 2012134392 A1 | 10/2012 | |
| WO | 2014060953 A1 | 4/2014 | |
| WO | 2014060959 A1 | 4/2014 | |
| WO | 2014060962 A1 | 4/2014 | |
| WO | 2015075601 A1 | 5/2015 | |

* cited by examiner

*Primary Examiner* — Jeffrey H Murray

(57) ABSTRACT

The present application provides pharmaceutical compositions derived from pemetrexed dipotassium Nonahydrate and its process thereof.

The present application also provides a method of treating cancer by administering intravenously the reconstituted lyophilized compositions into a patient in need thereof.

1 Claim, 1 Drawing Sheet

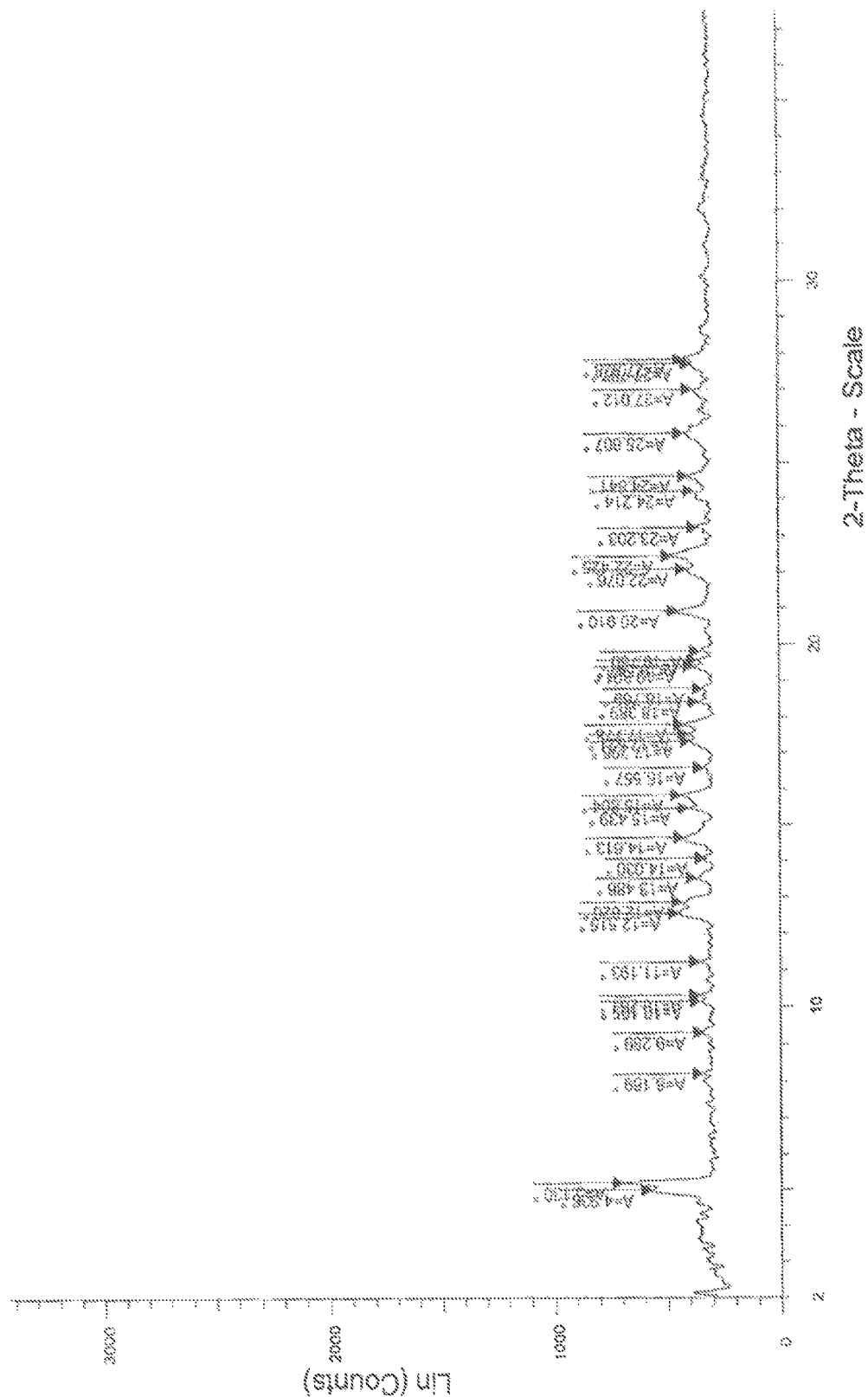

PEMETREXED DIPOTASSIUM FORMULATIONS

The present invention relates to pharmaceutical compositions derived from pemetrexed dipotassium Nonahydrate.

The present invention also relates to a process for preparing Pemetrexed dipotassium lyophilized compositions derived from pemetrexed dipotassium nonahydrate.

In other aspects the present invention relates to a method of treating cancer by administering intravenously the reconstituted lyophilized compositions of pemetrexed dipotassium, into a patient in need thereof.

INTRODUCTION

The chemical name of Pemetrexed is (S)-2-(4-(2-(2-amino-4-oxo-4,7-dihydro-3H-pyrrolo [2,3-d]pyrimidin-5-yl)ethyl)benzamido)pentanedioic acid and has the following chemical structure:

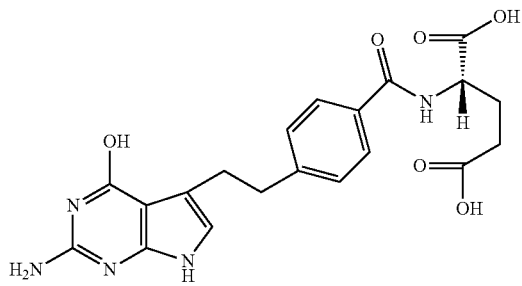

Pemetrexed disodium is the most common salt of pemetrexed di acid. Pemetrexed disodium heptahydrate is the active ingredient of Eli Lilly and Company's ALIMTA® injectable composition. Pemetrexed disodium heptahydrate has the following chemical structure:

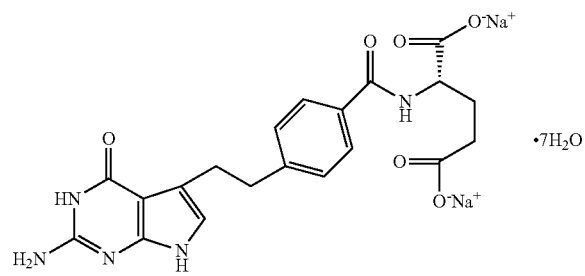

Pemetrexed disodium is a multi-targeted antifolate that strongly inhibits various folate-dependent enzymes, including thymidylate synthase (TS), dihydrofolate reductase (DHFR) and glycinamide ribonucleotide formyltransferase (GARFT). Pemetrexed disodium has been proved effective on a wide variety of solid tumors in clinical trials. Currently, pemetrexed disodium is commercial available in USA, European Union, Canada, Japan and China etc. for treatment of malignant pleural stromal tumor as a first-line drug, and local advanced and metastatic non-small cell lung cancer as a second-line drug. In the treatment of malignant pleural stromal turner, pemetrexed disodium is a unique chemotherapeutic agent in the market currently. In the second-line treatment of non-small cell lung cancer, pemetrexed disodium has a comparative efficacy and reduced toxicities compared with the standard drug Docetaxel. Hence, it is more likely for pemetrexed disodium to become a new standard treatment of the second-line treatment for non-small cell lung cancer. In addition, the clinical studies of pemetrexed disodium in the treatment of breast, bowel, pancreatic, head and neck, gastric and bladder cancers are still ongoing.

Riebesehl et al in U.S. Pat. No. 6,686,365 provides a pharmaceutical composition comprising pemetrexed, at least one antioxidant selected from the group consisting of monothioglycerol, L-cysteine, and thioglycolic acid, and a pharmaceutically acceptable excipient.

WO2008/021411A2 provide processes for the preparation of lyophilized pharmaceutically acceptable salts of pemetrexed diacid, in particular, pemetrexed disodium salt, directly from pemetrexed diacid or salts thereof, i.e., without isolating the obtained pemetrexed salt prior to lyophilizing it.

WO2010/030598 A2 application describes Pharmaceutical formulations comprising amorphous pemetrexed or its salts, and processes to prepare the formulations.

WO2012/015810 A2 discloses long term storage stable pemetrexed-containing liquid pharmaceutical compositions. The compositions can include pemetrexed or pharmaceutically acceptable salts thereof; an antioxidant selected from lipoic acid, dihydrolipoic acid, methionine and mixtures thereof; a chelating agent selected from lactobionic acid, sodium citrate, tribasic and mixtures thereof; and a pharmaceutically acceptable fluid. The pH of the compositions is in a range of about 8 to about 9.5 and total impurities in the range of less than about 5%.

CN 101081301 A1 discloses medicine composition containing pemetrexed, at least one kind of antioxidant as additive selected from L-arginine, L-glutathione, L-methionine and L-tryptophan, and pharmaceutically acceptable excipient.

CN 1907284 A1 discloses a pharmaceutical composition comprising pemetrexed, characterized in that to contain pemetrexed and stabilizer in composition, its weight ratio is 5:2-7.

Chelius et al in U.S. Pat. No. 7,138,521 describes a stable crystalline heptahydrate form of pemetrexed disodium salt. The patent states that pemetrexed can exist in the form of a heptahydrate which is more stable than the previously known 2.5 hydrate and shows that the primary advantage of the heptahydrate crystalline form over the 2.5 hydrate crystal form is its stability and also with respect to formation of related substances. It also shows that when the heptahydrate is subjected to elevated temperatures, low humidity, and/or vacuum, it is converted to the 2.5 hydrate (hemi-pentahydrate) crystal form by loss of water.

U.S. Pat. No. 8,088,919B2 provide crystalline forms of pemetrexed diacid, and processes for the preparation thereof.

CN 102838602A covers oxidation impurity compounds of pemetrexed or its salts thereof, namely, a pemetrexed oxide A, pemetrexed oxide B and its disodium salt compounds thereof.

WO2010031357A1 discloses new crystalline forms of pemetrexed diacid, as well as preparation methods thereof. WO2010031357A1 also cover the process of reacting Pemetrexed diacid with basic aqueous solutions to form pemetrexed salts like di-sodium salt, potassium salt, lithium salt and calcium salts.

WO2012134392A1 discloses a process of making a pemetrexed salt comprising a method for the preparation of crude pemetrexed disodium, which may be further, purified to pemetrexed disodium 2.5H$_2$O crystalline form.

CN 101417998 discloses a method for purifying a pemetrexed salt, and more specifically relates to the sodium salt of pemetrexed, includes a sodium salt, disodium salt, trisodium salt or the like.

WO2014060962A1 covers a pharmaceutical composition comprising pemetrexed di potassium hemiheptahydrate and a pharmaceutically acceptable amount of an excipient, wherein said composition is having moisture content less than 5% w/w.

Being pemetrexed as an important anticancer therapeutic agent, additional and improved ways of utilizing pemetrexed different salt/s may be of immense value to pharmaceutical science and the healthcare of cancer patients. Hence, there exists an apparent need in the development of new salt formulation and its process/es, which may be stable, commercially viable, safer for patient health, and with better and consistent quality parameters.

The present inventors have surprisingly found pharmaceutical compositions derived from Pemetrexed dipotassium Nonahydrate, which can be usable for intended therapeutic purposes.

SUMMARY OF INVENTION

Aspects of the present invention relates to a pharmaceutical composition derived from pemetrexed dipotassium nonahydrate characterized by X-ray powder diffraction pattern containing at least 5 characteristic 2θ° diffraction angle peaks selected from the XRPD peak set of 5.0, 12.5, 17.2, 20.8, 22.4, 25.7, 26.9 and 27.9±0.20 2θ°, and a pharmaceutically acceptable amount of an excipient, wherein the pharmaceutical composition having moisture content less than 2% w/w.

Specific aspects of the present invention relates to a lyophilized composition of Pemetrexed dipotassium, having moisture content less than 2% w/w, prepared from a prelyophilized composition comprising:
   a) about 10 mg/ml to about 100 mg/ml of pemetrexed di potassium nonahydrate calculated as pemetrexed, and
   b) about 10 mg/ml to about 200 mg/ml of Cryoprotectant, and a solvent.

In particular aspects of the present invention relates to a process for preparing a lyophilized composition of pemetrexed dipotassium, comprising the following steps:
   a) Dissolving a Cryoprotectant or a combination of Cryoprotectants in water for injection to form a solution;
   b) Dissolving pemetrexed dipotassium nonahydrate in to the above solution, and determining the pH of the solution;
   c) Adjusting the pH of the bulk solution to 7.2 by addition of pH adjusters.
   d) Make up the volume to 100% with WFI and stirred, and optionally determining the final pH of the solution.
   e) Optionally, filtering the solution obtained in step d) through 0.2μ filter to obtain a filtered solution;
   f) Freezing the solution obtained in step e) to form a frozen solution; and
   g) Drying to form the lyophilized composition, wherein the composition is having moisture content of less than 2% w/w.

Aspects of the present invention relates to a reconstituted lyophilized composition of Pemetrexed Dipotassium, where in the composition is reconstituted in 0.9% w/v Sodium Chloride Injection (preservative free).

Aspects of the present invention relates to a method of treating a patient for cancer comprising reconstituting a lyophilized composition of Pemetrexed dipotassium in normal saline, to form a reconstituted composition which is free of visual particles; and injecting the reconstituted composition intravenously into a patient.

BRIEF DESCRIPTION OF THE DRAWING

FIG. 1 is Illustration of X-ray powder diffraction (XRPD) pattern of Pemetrexed dipotassium nonahydrate.

DETAILED DESCRIPTION

As set forth herein, aspects of the present invention describe a pharmaceutical composition comprising pemetrexed dipotassium, and process for the preparation thereof.

The pharmaceutical composition used in the context of the present application refers to any one of several dosage forms suitable for administration of a drug, such as intraperitoneal, intravenous, intra-arterial, intramuscular, subcutaneous, oral etc.

In one of the embodiments of the present invention, describes a pharmaceutical composition derived from pemetrexed dipotassium nonahydrate characterized by X-ray powder diffraction pattern containing at least 5 characteristic 2θ° diffraction angle peaks selected from the XRPD peak set of 5.0, 12.5, 17.2, 20.8, 22.4, 25.7, 26.9 and 27.9±0.20 2θ°, and a pharmaceutically acceptable amount of an excipient, wherein the pharmaceutical composition having moisture content less than 2% w/w.

As described in FIG. 1 the characteristic XRPD 2θ° peaks and the respective d spacing values of Pemetrexed dipotassium nonahydrate are tabulated below.

| Angle (2θ°) ±0.20 | d Spacing Value (A°) |
|---|---|
| 4.94 | 17.888 |
| 5.13 | 17.211 |
| 8.17 | 10.814 |
| 9.29 | 9.512 |
| 10.10 | 8.746 |
| 10.26 | 8.614 |
| 11.19 | 7.898 |
| 12.51 | 7.067 |
| 12.83 | 6.896 |
| 13.49 | 6.560 |
| 14.03 | 6.307 |
| 14.61 | 6.056 |
| 15.49 | 5.734 |
| 15.80 | 5.603 |
| 16.56 | 5.349 |
| 17.30 | 5.123 |
| 17.52 | 5.057 |
| 17.78 | 4.985 |
| 18.39 | 4.820 |
| 18.77 | 4.723 |
| 19.39 | 4.573 |
| 19.55 | 4.537 |
| 19.78 | 4.484 |
| 20.91 | 4.245 |
| 22.08 | 4.023 |
| 22.42 | 3.961 |
| 23.20 | 3.830 |
| 24.21 | 3.672 |
| 24.64 | 3.609 |
| 25.81 | 3.449 |
| 27.01 | 3.298 |
| 27.71 | 3.217 |
| 27.83 | 3.203 |

A pharmaceutical composition of the present invention is derived from Pemetrexed Dipotassium Nonahydrate having water content in the range between 23 to 25.5% w/w.

In particular, one of the embodiments of the present invention provides a pharmaceutical composition derived from pemetrexed di potassium nonahydrate, and a pharmaceutically acceptable amount of an excipient, effective to form a lyophilized powder for injection. The lyophilized powder for injection particularly contain at least one or more Cryoprotectants.

In one of the particular embodiments of the present invention, describes a lyophilized composition of Pemetrexed dipotassium, having 155.73 mg pemetrexed di potassium nonahydrate, calculated as equivalent to 100 mg of pemetrexed, and 100 mg of mannitol; wherein the lyophilized composition having moisture content less than 2% w/w.

In one of the particular embodiments of the present invention, describes a lyophilized composition comprising 778.64 mg pemetrexed di potassium nonahydrate, calculated as equivalent to 500 mg of pemetrexed, and 500 mg of mannitol; wherein the lyophilized composition having moisture content less than 2% w/w.

In one of the embodiments of the present invention describes a lyophilized composition of Pemetrexed dipotassium, having moisture content less than 2% w/w, prepared from a prelyophilized composition comprising:
  a) about 10 mg/ml to about 100 mg/ml of pemetrexed di potassium nonahydrate calculated as pemetrexed, and
  b) about 10 mg/ml to about 200 mg/ml of Cryoprotectant, and a solvent.

In one of the embodiments of the present invention describes a process for preparing a lyophilized composition of pemetrexed dipotassium, comprising the following steps:
  a) Dissolving a Cryoprotectant or a combination of Cryoprotectants in a solvent to form a solution.
  b) Dissolving pemetrexed dipotassium nonahydrate in to the above solution, and determining the pH of the solution;
  c) Adjusting the pH of the bulk solution to 7.2 by addition of pH adjusters.
  d) Make up the volume to 100% with WFI and stirred, and optionally determining the final pH of the solution.
  e) Optionally, filtering the solution obtained in step d) through 0.2μ filter to obtain a filtered solution;
  f) Freezing the solution obtained in step e) to form a frozen solution; and
  g) Drying to form the lyophilized composition, wherein the composition is having moisture content of less than 2% w/w.

The above sequential steps on the process for preparing a lyophilized composition of pemetrexed dipotassium are described in detail below:

Cryoprotectants used in step (a) are often also referred to as bulking agents, that have "generally regarded as safe" (GRAS) status from the United States Food and Drug Administration (FDA) are well known in the art of pharmaceutical lyophilization and tend to strengthen the structure of the resulting lyophilized cake. Bulking agents include saccharides, preferably monosaccharides or oligosaccharides, sugar alcohols, and mixtures thereof. More specifically, bulking agents used in the present invention include sucrose, dextrose, maltose, lactose, sorbitol, glycine, mannitol and dextran. A most preferred bulking agent is mannitol.

Solvents used in step (a) include Water for injection (WFI), DMSO, ethanol, acetonitrile and others. A most preferred solvent is WFI which has good solubility for most of the Cryoprotectants, as well as Pemetrexed Dipotassium Nonahydrate.

Particularly, if WFI is used for step (a), it may be taken in a little excess amount, for example, 110% w/w of the batch quantity, and if required nitrogen purging can be carried out to remove dissolved oxygen, and 90% w/w of the batch quantity of nitrogen purged WFI are collected, and then the cryoprotectants are completely dissolved under stirring for appropriate time, in 5-10 minutes. The addition of Pemetrexed Dipotassium Nonahydrate to the step (a) solution can be carried by gradual addition and desired stirring rate, to get a clear solution in 5-10 minutes.

The pH of the bulk solution (c) is measured and adjusted to 7.2 using acidic/basic pH adjusters like Hydrochloric acid/Potassium hydroxide respectively. Particularly, the pH adjustment can be carried out under constant stirring of the bulk solution and the pH limits to the target may be +/−0.02 units. After making the final volume of the bulk solution to 100% w/w in step (d), optionally, the pH checking can be done to ensure fee target pH of the solution to 7.2.

After the completion of bulk solution preparation and pH adjustment, the solution remains clear, however, in some instances, in order to remove the undissolved particulate matter, the solution can be filtered through 0.2μ PES filter, and the so obtained filtered solution is subjected to freeze-drying.

Lyophilization process (often referred to as Freeze-drying) is employed for certain injectable pharmaceuticals that may exhibit poor active ingredient stability in aqueous solutions. Lyophilization process is suitable for injectables because, it can be conducted under sterile conditions, which is a primary requirement for parenteral dosage forms. Cryoprotectants are excipients incorporated to protect the active constituent during a freezing process.

In freeze-drying process water is removed from a product after it is frozen and placed under a vacuum, allowing the ice to change directly from a solid to a vapor, without passing through a liquid phase. The process consists of three separate, unique, and interdependent processes; a freezing phase, a primary drying phase (sublimation), and a secondary drying phase (desorption). These processes may be optimized to enhance the product stability as well as decrease the manufacturing costs.

Freezing Phase:

A primary function of the freezing phase is to ensure that the entire container having the complex solution is completely frozen, prior to proceeding to a subsequent phase. Additionally, it is usually desired that these containers freeze in a uniform manner. While there are different ways that this can be accomplished, one option is to chill the containers after they are loaded onto the lyophilizer shelves and holding for 30-60 minutes prior to initiation of the freezing cycle. It is generally not practical to equilibrate the shelves to a freezing temperature, because of frost accumulation during the filling and loading of the containers.

Primary Drying Phase:

Once the formulation is brought to the desired frozen state, primary drying via sublimation can proceed. The primary drying phase involves the removal of bulk water at a product temperature below the ice transition temperature under a vacuum (pressures typically employed are between 0.2 to 0.33 Milli bar). This phase can be a critical one for stabilizing an active. The goal is to identify the glass transition temperature (Tg') for the formulation. The Tg' is the temperature at which there is a reversible change of state between a viscous liquid and a rigid, amorphous glassy state.

One can measure the Tg' of candidate formulations using a differential scanning calorimeter (DSC), in particular with modulated DSC. Generally, the collapse temperature is observed to be about 2-5° C. greater than the Tg'. Hence, the shelf temperature is set such that the target product temperature is maintained near or below the Tg' of the formulation throughout the removal of solvent during the primary dry phase.

As the solvent is progressively removed from the formulation containers, the product temperature will approach and reach the shelf temperature since it is no longer cooled by water sublimation. To optimize the duration of the primary dry phase, the removal of solvent vapor can be tracked using a moisture detector, or by monitoring the decrease in pressure difference between a capacitance manometer and a thermocouple pressure gauge or by a pressure drop measurement. The optimization of the primary dry cycle involves a removal of solvent as quickly as possible without causing cake collapse and subsequent product instability.

Secondary Drying Phase:

The secondary drying phase is the final segment of the lyophilization cycle, where residual moisture is removed from a formulation's interstitial matrix by desorption with elevated temperatures and/or reduced pressures. The final moisture content of a lyophilized formulation, which can be measured by Karl Fischer or other methods, is important because if the solid cake contains too much residual moisture, the stability of the active can be compromised. Hence, it is imperative that one achieves a moisture level as low as possible.

To accomplish a low residual moisture, the shelf temperature is typically elevated to accelerate desorption of water molecules. The duration of the secondary drying phase is usually short. When microstructure collapse occurs, the residual moisture is generally significantly greater than desired. One alternative is to purge the sample chamber of the lyophilizer with alternating cycles of an inert gas such as nitrogen, to facilitate displacement of bound water. However, another solution is to properly formulate the drug product and run an optimal lyophilization cycle.

The advantages of lyophilization include: ease of processing a liquid, which simplifies aseptic handling; enhanced stability of a dry powder; removal of water without excessive heating of the product; enhanced product stability in a dry state; and rapid and easy dissolution of reconstituted product. The product is dried without elevated temperatures, thereby eliminating adverse thermal effects, and then stored in the dry state in which there are relatively few stability problems.

Additionally, freeze dried products are often more soluble, dispersions are stabilized, and products subject to degradation by oxidation or hydrolysis are protected.

A pharmacologically active constituent of many pharmaceutical products is present in such small quantities that, if freeze dried alone, it may not give a composition of suitable mass, and in some cases its presence would be hard to detect visually. Therefore, excipients are often added to increase the amount of solids present. In most applications it is desirable for a dried product cake to occupy essentially the same volume as that of the original solution. To achieve this, the total solids content of the original solution is frequently about 10 to 25% by weight.

In one of the particular embodiments of the present invention, it describes a sterile vessel containing pemetrexed dipotassium for administration to a subject in need thereof.

The sterile vessel containing a pharmaceutical formulation according to the present invention may be a vial, syringe, or ampoule.

In the present invention, the reconstitution of lyophilized composition of Pemetrexed dipotassium 100 mg/vial, to be done in 0.9% w/v of Sodium Chloride Injection (preservative free) ranging about 4 to 5 ml, similarly for 500 mg/vial, the reconstitution can be carried out with about 18 to 25 ml.

In the present invention, the pH of reconstituted lyophilized composition of Pemetrexed dipotassium has a pH ranging between 6 to 8. Preferably, between 7 to 8.

In one of the particular embodiments of the present invention, it describes a method for treating a patient for cancer comprising: reconstituting a lyophilized composition of Pemetrexed dipotassium, with 0.9% w/v Sodium Chloride injection (preservative free), to form the reconstituted pharmaceutical composition that is free of visual particles; and injecting the reconstituted composition intravenously into a patient.

Owing to the advantage of compositions of the present invention a reconstitution solution devoid of sodium content may provide cardio protective role for the patients suffering with cardiac disorders due to use of sodium ion.

Particular embodiments of the present invention provide kits for delivery of the pemetrexed or its salts. A kit according to the present invention comprises a container holding the drug composition, a sterile reconstitution vehicle, and a sterile syringe.

Certain specific embodiments of the invention will be further described in the following examples, which are provided only for purposes of illustration and are not intended to limit the scope of the invention in any manner.

Usage of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The term wt % refers to percent by weight. All methods described herein can be performed in any suitable order unless otherwise indicated herein or otherwise clearly contradicted by context. The use of any and all examples or exemplary language (e.g. "such as") provided herein, is intended merely to better illuminate the invention and does not pose a limitation on the scope of the invention unless otherwise claimed. No language in the specification should be construed as indicating any non-claimed element as essential to the practice of the invention.

The term "about" is a value that can be considered +/−5% of the given value.

Particular embodiments of this invention are described herein, including the best mode known to the inventors for carrying out the invention. Variations of those particular embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Certain specific aspects and embodiments of the present application will be explained in more detail with reference to the following examples, which are provided by way of illustration only and should not be construed as limiting the scope of the invention in any manner.

EXPERIMENTAL DETAILS

Example 1: Pemetrexed Dipotassium Nonahydrate Form-SP9 is Prepared by the Example as Given Below a) 125 mL of DM water was charged in to 1 Liter RB flask at room temperature and under stirring 31 g Pemetrexed Dipotassium was added to it.

b) The reaction mixture was stirred for 20 minutes to obtain a clear solution, which was then filtered through a micron filter paper.

c) The filtrate obtained was then charged into another RB flask and under continuous stirring it was cooled to 0° C.

d) To the cooled reaction mixture 430 mL of ethanol was added drop-wise within 60 min, with continuous stirring.

e) From the reaction mass obtained, the compound was filtered and suck dried for ~10 minutes. The partially dried solid material was then washed with 65 mL of ethanol. The solid material was then suck dried for ~30 minutes and the obtained partially wet compound was loaded into f) Another RB flask followed by addition of 160 mL acetone. The reaction mass was stirred for 1 hr at ~25° C. Then the compound obtained was filtered, washed with 35 mL acetone, suck dried for ~10 minutes and unloaded to obtain the title compound.

Yield: 23.5 g, 76.66%
HPLC purity: 99.91%
Water content (by KF): 24.78% w/w

Example 2-3: Pemetrexed Di Potassium Nonahydrate Composition

| S. No. | Ingredients | Example 2 100 mg/vial | Example 3 500 mg/vial |
|---|---|---|---|
| 1 | Pemetrexed Dipotassium nonahydrate | 155.73 mg | 778.64 |
| 2 | Mannitol | 100 mg | 500 mg |
| 3 | Potassium hydroxide/ Hydrochloric acid | Q.s to adjust the pH 7.2 | |
| 4 | Water for injection | q.s to 4.0 mL | q.s to 20 mL |

Manufacturing Process a) 110% of required amount of WFI is subjected to nitrogen purging in a storage vessel. 90% of the batch quantity of nitrogen purged WFI is taken for the batch.

b) Dissolving Mannitol in WFI of step (a) to get clear solution.

c) Dissolving pemetrexed dipotassium nonahydrate to the solution of step (b), and adjusting the pH of the bulk solution to 7.2 by addition of pH adjusters, Potassium hydroxide/ Hydrochloric acid.

d) Make up the final volume of the above bulk solution to 100% with WFI and stirred, and checking the pH of the solution.

e) Optionally, filtering the solution obtained in step d) through 0.2μ filter to obtain a filtered solution;

f) Freezing the solution obtained in step e) to form a frozen solution; and g) Freeze drying the frozen solution to form the lyophilized composition, wherein the composition is having moisture content less than 2% w/w.

Lyophilization Recipe

| Stage | Temperature (° C.) | Ramp (Minutes) | Hold (minutes) | Vacuum (mbar) |
|---|---|---|---|---|
| Freezing | −15 | 60 | 60 | — |
| Primary drying | −40 | 60 | 180 | — |
|  | −40 | — | 5 | 0.33 |
|  | −15 | 120 | 400 | 0.33 |
|  | −5 | 60 | 300 | 0.33 |
|  | 5 | 60 | 300 | 0.2 |
|  | 25 | 60 | 500 | 0.2 |
| Secondary drying | 40 | 60 | 600 | 0.06 | h) After completion of lyophilization, the vacuum is released by introduction of nitrogen and then vials are stoppered completely by hydraulic pressing. The vials are further sealed with flip-off seals.

i) The vials are cleaned externally and stored at 15-30° C.

The lyophilized vials of Example 2 and 3 are analyzed for pH after reconstituting in 0.9% Sodium Chloride Injection (preservative free) and Water content of Lyophilized powder analyzed by Karl-Fisher method.

The results are tabulated below:—

| Parameter | Example 2 Initial | Example 3 Initial |
|---|---|---|
| pH | ~7.2 | ~7.2 |
| Water content of Lyophilized powder (Karl-Fischer) (% w/w) | 1.09 | 1.19 |

The abovementioned examples, which are provided by way of illustration, should not be construed as limiting the scope of the invention with respect to parameter/s, ingredient/s and quantities used in any manner.

The invention claimed is:

1. A pharmaceutical composition comprising pemetrexed dipotassium nonahydrate characterized by X-ray powder diffraction pattern containing at least 5 characteristic 2θ° diffraction angle peaks selected from the XRPD peak set of 5.0, 12.5, 17.2, 20.8, 22.4, 25.7, 26.9 and 27.9±0.20 2θ°, and a pharmaceutically acceptable amount of an excipient, wherein the pharmaceutical composition having moisture content less than 2% w/w.

* * * * *